United States Patent
Berrebi-Bertrand et al.

(10) Patent No.: US 12,134,608 B2
(45) Date of Patent: Nov. 5, 2024

(54) BENZIMIDAZOLE DERIVATIVES AS DUAL HISTAMINE H1 AND HISTAMINE H4 RECEPTOR LIGANDS

(71) Applicant: BIOPROJET, Paris (FR)

(72) Inventors: Isabelle Berrebi-Bertrand, Pace (FR); Xavier Billot, Saint-Grégoire (FR); Thierry Calmels, Rennes (FR); Marc Capet, Melesse (FR); Stéphane Krief, Rennes (FR); Olivier Labeeuw, Fougeres (FR); Jeanne-Marie Lecomte, Paris (FR); Nicolas Levoin, L'Hermitage (FR); Xavier Ligneau, Saint-Grégoire (FR); Philippe Robert, Pace (FR); Jean-Charles Schwartz, Paris (FR)

(73) Assignee: BIOPROJET, Paris (FR)

( * ) Notice: Subject to any disclaimer, the term of this patent is extended or adjusted under 35 U.S.C. 154(b) by 0 days.

(21) Appl. No.: 17/668,575

(22) Filed: Feb. 10, 2022

(65) Prior Publication Data
US 2022/0281839 A1 Sep. 8, 2022

Related U.S. Application Data

(62) Division of application No. 16/192,162, filed on Nov. 15, 2018, now Pat. No. 11,306,069.

(30) Foreign Application Priority Data

Nov. 15, 2017 (EP) ..................................... 17306587

(51) Int. Cl.
| | |
|---|---|
| *C07D 401/12* | (2006.01) |
| *A61K 31/454* | (2006.01) |
| *A61K 45/06* | (2006.01) |
| *A61P 29/00* | (2006.01) |
| *A61P 37/08* | (2006.01) |

(52) U.S. Cl.
CPC .......... *C07D 401/12* (2013.01); *A61K 31/454* (2013.01); *A61K 45/06* (2013.01); *A61P 29/00* (2018.01); *A61P 37/08* (2018.01)

(58) Field of Classification Search
CPC .... C07D 401/12; A61K 31/454; A61K 45/06; A61P 37/08; A61P 29/00
See application file for complete search history.

(56) References Cited

U.S. PATENT DOCUMENTS

| | | | |
|---|---|---|---|
| 6,683,191 B2 | 1/2004 | Deng et al. | |
| 8,802,664 B2* | 8/2014 | Berrebi-Bertrand .... | A61P 15/10 546/198 |
| 9,029,357 B2* | 5/2015 | Berrebi-Bertrand .... | A61P 11/00 514/253.09 |
| 2002/0077483 A1 | 6/2002 | Deng et al. | |
| 2005/0090527 A1 | 4/2005 | Anthes et al. | |
| 2013/0231329 A1 | 9/2013 | Berrebi-Bertrand et al. | |
| 2015/0004181 A1 | 1/2015 | Berrebi-Bertrand et al. | |

OTHER PUBLICATIONS

Waldeck, B., Biological Significance of the Enantiomeric Purity of Drugs, 5 Chirality 350-355 (1993) (Year: 1993).*
European Search Report for EP 18286553 dated Nov. 30, 2018.
Koechling, et al., "Combined treatment with H1 and H4 receptor antagonists reduces inflammation in a mouse model of atopic dermatitis", Journal of Dermatological Science, vol. 87, (Apr. 12, 2017), pp. 130-137.
Hammer, et al., "2, 4-Diaminopyrimidines as dual ligands at the histamine H1 and H4 receptor—H1/H4—receptor selectivity", Bioorganic & Medicinal Chemistry Letters, vol. 26, (Dec. 11, 2015), pp. 292-300.
Wagner, et al., "Pharmacological profile of astemizole-derived compounds at the histamine H1 and H4 receptor—H1/H4 receptor selectivity", Naunyn-Schmiedeberg's Arch Pharmacol, (Nov. 17, 2013), pp. 235-250.
Zampeli, et al., "The role of histamine H4 receptor in immune and inflammatory disorders", British Journal of Pharmacology, vol. 157, (Mar. 20, 2009), pp. 24-33.
Nakano, et al., "The role of histamine H4 receptor in allergic conjunctivitis in mice", European Journal of Pharmacology, vol. 608, (Feb. 26, 2009), pp. 71-75.
Hiroshi Yamanaka and Yasuhisa Tashiro, "General Aspects of the Preparation of Optically Active Compounds", 1998.
Kazuhide Serizawa, "The Science of Polymorphism and Crystallization of Medicaments," 2002, pp. 57-102 and 305-317.
Kato, Gekkan Yakuji, The Pharmaceuticals Monthly, vol. 29, No. 10, (Oct. 1, 1987), pp. 23-26.
Hirayama: "Yuki Kagobutsu Kessho Sakusei Handbook", 2008, Kodansha Ltd, Tokyo, ISBN: 978-4-621-07991-1.
Hiryuki Nohira, Editor, "Optically active substances: their industrial organic chemistry" Asakura Shoten, publisher (1989), ISBN 978-4-254-14551-9.

* cited by examiner

*Primary Examiner* — Timothy R Rozof
(74) *Attorney, Agent, or Firm* — Aaron Schulman, Esq.; Stites & Harbison, PLLC

(57) ABSTRACT

The present application concerns novel benzimidazole enantiomeric derivatives, their process of preparation and their therapeutical uses as dual H1 and H4 receptor ligands.

18 Claims, 2 Drawing Sheets

BENZIMIDAZOLE DERIVATIVES AS DUAL HISTAMINE H1 AND HISTAMINE H4 RECEPTOR LIGANDS

CROSS REFERENCE TO RELATED APPLICATIONS

This application is a Divisional application of U.S. application Ser. No. 16/192,162, filed Nov. 15, 2018, which is based on and claims priority to EP 17306587.1, filed Nov. 15, 2017, all of said applications being incorporated herein by reference.

FIELD

The present patent application concerns new ligands of the H4-receptor, their process of preparation and their therapeutic use.

BACKGROUND

The histamine H4 receptor (H4R) belongs to the superfamily of G-protein coupled heptahelical receptors and is expressed on the plasma membranes of a variety of immunocompetent/inflammatory cells, e.g. eosinophils, basophils, mast-cells or dendritic cells. The H4R has a chemiotactic role, controlling the afflux of e.g. mast-cells or eosinophils to inflammatory sites that is elicited by histamine release and, thereby plays a major role in the development of chronic inflammatory disorders. It also controls the activity of eosinophils and some classes of lymphocytes. Blockade of the H4R by antagonists or inverse agonists should therefore constitute a novel therapeutic approach in diseases like asthma, emphysema, allergic rhinitis, nasal congestion, bronchitis, chronic obstructive pulmonary disease, dermatitis, arthritis, psoriasis, colitis, etc. in which they could be used alone or in association with already used other classes of anti-inflammatory medications, namely H1R antagonists. In addition, the use of H4R antagonists/inverse agonists is also of potential interest in a variety of autoimmune diseases e.g. type I diabetes, Crohn's disease, multiple sclerosis, lupus, etc. . . . . The itch-preventing effect of some H4R antagonists in a rodent model (Bell et al, Br J Pharmacol, 2004, 142, 374) also suggests the use of these agents in pruritus.

Patent application WO2012/041860 describes compounds of the following general formula (I):

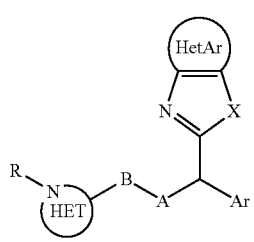

(I)

as antagonists and/or inverse agonists of H4 human receptor.

The histamine H1 receptor (H1R) belongs to the superfamily of G-protein coupled heptahelical receptors. The activation of H1 receptors in blood vessels and nerve endings is responsible for many of the symptoms of allergic rhinitis, allergic conjunctivitis, contact dermatitis, atopic dermatitis, ocular itching, chronic urticaria, eczema, prurigo, pruritus cutaneous, psoriasis vulgaris, anaphylactic shock and erythema exsudativum.

H1-antihistamine compounds are at least partly effective in treating these diseases or symptoms.

Compounds displaying activity as antagonists or inverse agonists at both human H1 and H4 receptors may thus be active against numerous pathologies: anaphylactic shock, respiratory inflammatory and allergic diseases, adult respiratory distress syndrome, acute respiratory distress syndrome, respiratory infections, bronchitis, chronic bronchitis, chronic obstructive pulmonary disease, cystic fibrosis, asthma, emphysema, rhinitis, rhinorrhea, chronic sinusitis (rhinosinusitis), allergy, allergy induced airway responses, allergic rhinitis, viral rhinitis, non-allergic rhinitis, perennial and seasonal rhinitis, conjunctivitis, allergic conjunctivitis, nasal congestion, allergic congestion, otitis, nasal polyps, cough, female and male sexual dysfunction, overactive bladder conditions, urinary incontinence, bladder overactivity, benign prostate hyperplasia, lower urinary tract syndrome, dermatitis, atopic dermatitis, psoriasis, itchy skin, pruritus, urticaria, chronic urticaria, skin incision model of postoperative pain, allergic skin disease/itching and inflammation, allergic contact dermatitis, thromboembolic diseases, atherosclerosis, myocardial infarction, angina pectoris, myocardial ischemia, arrhythmia, peripheral arterial occlusive diseases, pulmonary embolism, deep venous thromboses, hypotension, pulmonary hypertension, angioedema, malignant hypertension, cardiac insufficiency, heart or kidney failure, stroke and renal dysfunction, inflammatory bowel disease, Crohn's disease, ulcerative colitis, intestinal anaphylaxis, food allergy, post inflammatory visceral hypersensitivity, peritonitis, rheumatoid arthritis, multiple sclerosis, lupus, osteoarthritis joint pain, general inflammation, cancer, neuropathic pain, chronic hyper-eosinophilias, chronic diseases associated with mast cell multiplication, etc.

Dual H4R-H1R antagonists/inverse agonists are thus of great interest as the combination of the two properties would improve the therapeutic efficiency of the compound. So far this has only been explored with combinations as no suitable dual H4R-H1R antagonists/inverse agonists is currently available. For example, both JNJ7777120 (H4R ligand) and the H1R antagonist levocabastine inhibited eye scratching behavior and the combination of the two agents caused even more potent inhibition in allergic conjunctivitis (Nakano Y et al. Eur J Pharmacol 2009; 608:71-5). A combination of JNJ-39758979 (H4R antagonist) and mepyramine (H1R inverse agonist) showed synergistic activity in a mouse model of atopic dermatitis (Köchling H et al J. Dermatol. Sci. 2017; 87; 130-137), might be a treatment for pruritus (Exp. Dermatol. 18; 2009; 57-63), intestinal anaphylaxis (Wang M et al Allergy 71; 2016; 1561-1574), allergic contact dermatitis (Matsushita A et al Exp Dermatol. 21; 2012; 714-5).

No dual H1R-H4R antagonists/inverse agonist has yet reached clinical uses and there is therefore a need for such dual compounds displaying high potency and safety.

SUMMARY OF THE INVENTION

The present application concerns a novel chemical class of dual H1R-H4R ligands and relates to novel benzimidazoles derivatives as dual H1-H4 receptor antagonists or inverse agonists, to their preparation, and to their application in therapeutics.

The inventors have surprisingly found that some enantiomers having a defined stereochemistry of the derivatives disclosed in WO2012/041860 display antagonist and/or inverse agonist activity at the human H1 receptor in addition to the disclosed H4 activity. In other words, the enantiomer having said defined stereochemistry, typically the (S) enantiomer, displays activity for both the human H1 receptor and the human H4 receptor. This is extremely interesting as the activity on both the H1 receptor and the H4 receptor expands the therapeutic utility of the compounds onto inflammatory disorders and allergic disorders.

Still further, it has been totally unexpectedly found that the enantiomer which proved to be the most active on the human H4 receptor (eutomer) is also the most active on the human H1 receptor, whereas the enantiomer which is the less active on the human H4 receptor (distomer) is also the less active on the human H1 receptor.

DETAILED DESCRIPTION OF THE INVENTION

The general formula of these enantiomers is general formula (II):

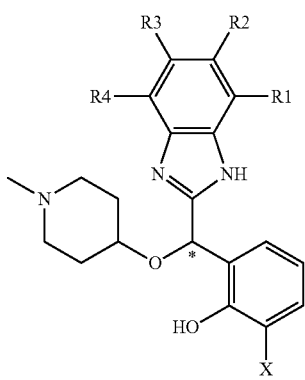

(II)

wherein:
* denotes the asymmetric carbon exhibiting the defined stereochemistry, typically the (S) stereochemistry
X represents H or F;
R1, R2, R3, and R4 identical or different independently represent H, halogen, alkyl or alkoxy;
Wherein one of X, R1, R2, R3, and R4 does not represent H;
as well as their pharmaceutically acceptable salts, tautomers, hydrates and solvates.

Compounds of formula (II) are new. WO2012/041860 does not describe any of these specific enantiomers having the defined stereochemistry as defined above.

Unless specified otherwise, the terms used hereabove or hereafter have the meaning ascribed to them below:

"Halo" or "halogen" refers to fluorine, chlorine, bromine or iodine atom.

"Alkyl" represents an aliphatic-hydrocarbon group which may be straight or branched having 1 to 20 carbon atoms in the chain unless specified otherwise. Preferred alkyl groups have 1 to 12 carbon atoms, more preferably have 1 to 6, or 1 to 4 carbon atoms in the chain; lower alkyls have preferably 1 to 4 carbon atoms. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alkoxy" refers to —O-Alkyl where Alkyl is defined as above.

In one preferred embodiment, the present invention provides a compound selected from the group consisting of:
(S)-2-[(1H-benzimidazol-2-yl)(1-methylpiperidin-4-yloxy) methyl]-6-fluorophenol
(S)-2-[(1H-benzimidazol-2-yl)(1-methylpiperidin-4-yloxy) methyl]-6-fluorophenol, hydrochloride, monohydrate
2-[(5-chloro-4-fluoro-1H-benzimidazol-2-yl)(1-methylpiperidin-4-yloxy)methyl]phenol enantiomer B
2-[(4-methyl-1H-benzimidazol-2-yl)(1-methylpiperidin-4-yloxy)methyl]phenol enantiomer B
2-[(5-fluoro-1H-benzimidazol-2-yl)(1-methylpiperidin-4-yloxy)methyl]phenol enantiomer B
2-[(4-chloro-1H-benzimidazol-2-yl)(1-methylpiperidin-4-yloxy)methyl]phenol enantiomer B
2-[(5-chloro-4-methyl-1H-benzimidazol-2-yl)(1-methylpiperidin-4-yloxy)methyl]phenol enantiomer B
(S)-2-[(1H-benzimidazol-2-yl)(1-methylpiperidin-4-yloxy) methyl]-6-fluorophenol, hydrochloride
(S)-2-[(1H-benzimidazol-2-yl)(1-methylpiperidin-4-yloxy) methyl]-6-fluorophenol, (R)-para-methylmandelate,
And in particular
(S)-2-[(1H-benzimidazol-2-yl)(1-methylpiperidin-4-yloxy) methyl]-6-fluorophenol
(S)-2-[(1H-benzimidazol-2-yl)(1-methylpiperidin-4-yloxy) methyl]-6-fluorophenol, hydrochloride, monohydrate
(S)-2-[(5-chloro-4-fluoro-1H-benzimidazol-2-yl)(1-methylpiperidin-4-yloxy)methyl]phenol
(S)-2-[(4-methyl-1H-benzimidazol-2-yl)(1-methylpiperidin-4-yloxy)methyl]phenol
(S)-2-[(5-fluoro-1H-benzimidazol-2-yl)(1-methylpiperidin-4-yloxy)methyl]phenol
(S)-2-[(4-chloro-1H-benzimidazol-2-yl)(1-methylpiperidin-4-yloxy)methyl]phenol
(S)-2-[(5-chloro-4-methyl-1H-benzimidazol-2-yl)(1-methylpiperidin-4-yloxy)methyl]phenol
(S)-2-[(1H-benzimidazol-2-yl)(1-methylpiperidin-4-yloxy) methyl]-6-fluorophenol, hydrochloride
(S)-2-[(1H-benzimidazol-2-yl)(1-methylpiperidin-4-yloxy) methyl]-6-fluorophenol, (R)-para-methylmandelate,
as well as their enantiomers, diastereomers, mixtures thereof and pharmaceutically acceptable salts, free forms, tautomers, hydrates and solvates.

The "B" enantiomer disclosed herein is the one of the two enantiomers of the defined stereochemistry for a given racemic structure, that exhibits the higher activity with respect to both the H4 and H1 receptors.

Typically, this enantiomer is the one of the two enantiomers that has the higher retention time when conducting a chiral HPLC analysis on the racemic mixture, for example when the chiral HPLC is conducted on an analytical chiral pack AD-H 250×4.6 mm column, with an eluting mixture comprising heptane/isopropanol, and diethylamine (0.1%), at a flow of 1 ml/min.

As used herein, "enantiomer B" typically refers to the (S) enantiomer.

As used herein, "enantiomer A" typically refers to the (R) enantiomer.

The compounds of the invention may also comprise tautomeric forms which are all encompassed by the present invention. In particular, in formula (II), the benzimidazole may have tautomeric forms: 1H-benzimidazole is a tautomer of 3H-benzimidazole. A representative example is illustrated below:

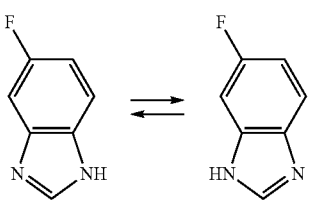 [SMILES: Fc1ccc2[nH]cnc2c1 ; Fc1ccc2nc[nH]c2c1]

The compounds of formula (II) can be provided in the form of a free base or in the form of addition salts with acids, which also form part of the invention.

These salts are advantageously prepared with pharmaceutically acceptable acids, but salts with other acids, useful for example for the purification or for the isolation of the compounds of formula (II), also form part of the invention.

According to an embodiment, the compound of formula (II) is (S)-2-[(1H-benzimidazol-2-yl)(1-methylpiperidin-4-yloxy)methyl]-6-fluorophenol, hydrochloride.

Said hydrochloride may comprise various polymorphs, in its anhydrous or solvated/hydrated states.

According to an embodiment, said polymorph in the anhydrous state, herein called form I, comprises the following peaks in the X-ray powder diffraction, typically measured with a PANALYTICAL X'PERT PRO MPD diffractometer apparatus under the following conditions:
    transmission mode
    record between 2° and 50°
Characteristic peaks of the anhydrous state are the followings:

| Angle 2θ (°) | Interreticular distance d (Å) | Intensity (cts) | Relative intensity (%) |
|---|---|---|---|
| 8.63 | 10.24 | 2479 | 28 |
| 11.05 | 8.00 | 1607 | 18 |
| 11.37 | 7.78 | 1924 | 22 |
| 12.42 | 7.12 | 1796 | 20 |
| 13.07 | 6.77 | 4268 | 48 |
| 14.48 | 6.11 | 4577 | 52 |
| 15.89 | 5.57 | 7181 | 81 |
| 16.82 | 5.27 | 8824 | 100 |
| 17.91 | 4.95 | 1149 | 13 |
| 18.79 | 4.72 | 1190 | 13 |
| 19.06 | 4.65 | 1361 | 15 |
| 19.91 | 4.46 | 4937 | 56 |
| 20.44 | 4.34 | 1172 | 13 |
| 21.28 | 4.17 | 4579 | 52 |
| 22.31 | 3.98 | 641 | 7 |
| 22.75 | 3.91 | 903 | 10 |
| 23.41 | 3.80 | 1196 | 14 |
| 24.49 | 3.63 | 738 | 8 |
| 25.04 | 3.55 | 2248 | 25 |
| 25.51 | 3.49 | 536 | 6 |
| 25.74 | 3.46 | 1235 | 14 |
| 26.26 | 3.39 | 2231 | 25 |
| 26.90 | 3.31 | 2021 | 23 |
| 27.32 | 3.26 | 435 | 5 |
| 27.63 | 3.23 | 1078 | 12 |
| 28.40 | 3.14 | 1619 | 18 |
| 29.44 | 3.03 | 720 | 8 |
| 30.13 | 2.96 | 1869 | 21 |
| 30.67 | 2.91 | 485 | 5 |
| 32.26 | 2.77 | 676 | 8 |
| 32.84 | 2.73 | 457 | 5 |
| 35.68 | 2.51 | 683 | 8 |
| 36.30 | 2.47 | 661 | 7 |

According to an embodiment, said polymorph in the hydrated state herein called form II is a monohydrate form and comprises the following peaks in the X-ray powder diffraction, typically measured with a PANALYTICAL X'PERT PRO MPD diffractometer apparatus under the following conditions:
    transmission mode
    record between 2° and 50°
Characteristic peaks of the monohydrate state are the followings:

| Angle 2θ (°) | Interreticular distance d (Å) | Intensity (cts) | Relative intensity (%) |
|---|---|---|---|
| 6.26 | 14.11 | 2415 | 25 |
| 10.99 | 8.04 | 2785 | 28 |
| 11.25 | 7.86 | 1852 | 19 |
| 13.66 | 6.48 | 4987 | 51 |
| 14.45 | 6.13 | 1922 | 20 |
| 15.12 | 5.86 | 3307 | 34 |
| 15.67 | 5.65 | 9787 | 100 |
| 16.40 | 5.40 | 2500 | 26 |
| 18.12 | 4.89 | 4652 | 48 |
| 19.17 | 4.63 | 1152 | 12 |
| 20.25 | 4.38 | 7744 | 79 |
| 21.01 | 4.23 | 684 | 7 |
| 22.09 | 4.02 | 2582 | 26 |
| 22.66 | 3.92 | 617 | 6 |
| 24.45 | 3.64 | 2303 | 24 |
| 27.58 | 3.23 | 5171 | 53 |
| 29.13 | 3.06 | 1381 | 14 |
| 33.14 | 2.70 | 796 | 8 |

According to a further object, the present invention is also concerned with the process of preparation of the compounds of formula (II).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, keto, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, methylcyclohexane, toluene and xylene; amides, such as N,N-dimethylformamide; alcohols such as ethanol and methanol and ethers, such as diethyl ether, methyl tert-butyl ether, methyl cyclopentyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

Typically, the enantiomers of formula (II) of the invention may be prepared by enantiomeric separation of the corresponding racemic mixtures.

The separation of the two enantiomers may be performed by chiral chromatography including simulated moving bed chromatography, salt formation with chiral agents, diastereomer formation with chiral copules, and preferential crystallization.

The racemates of the compounds of formula (II) can be prepared by application of the methods disclosed in WO2012/041860. More particularly, they may be prepared, according to an embodiment by etherification of compound of formula (III):

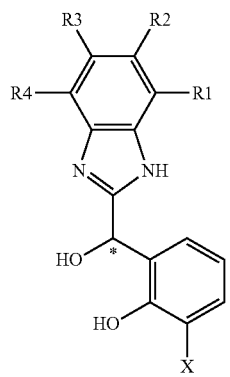

in which X, R1, R2, R3, R4 are as defined in general formula (II)

with a compound of formula (IV):

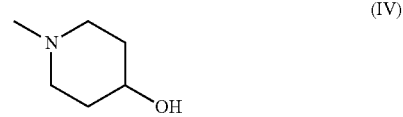

This etherification reaction can be performed in acidic medium (toluenesulfonic acid, methanesulfonic acid) in an inert solvent (toluene, chlorobenzene, dichloroethane) at a temperature between room temperature and about 160° C.

Compounds of formula (III) can be prepared by application of the methods disclosed in WO2012/041860.

Alternatively, according to another embodiment compounds of formula (I) can be prepared by methylation of compound of formula (V):

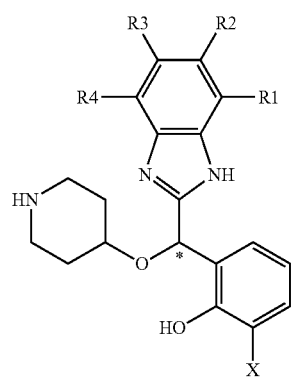

in which R1, R2, R3, R4, X are as defined in general formula (II)

This methylation can be performed by reductive method using a carbonylated compound and a reducing agent such as a borohydride, a cyanoborohydride, a triacetoxyborohydride, hypophosphonous acid, formic acid, formic acid/triethylamine or hydrogen, a catalyst such as palladium can be added for this transformation when hydrogen or hydrogen donors are used.

Compounds of formula (V) can be prepared according to the methods disclosed in WO 2012/041860.

Furthermore, compounds of formula (III) can be prepared from compounds of formula (II) by group interconversion or group transformation. Such reaction include, but are not limited to, reaction on aromatic or heteroaromatic groups such as halogen exchange reaction, copper catalyzed ether formation, Sonogashira reaction, Heck reaction, Suzuki reaction, sulfide condensation, triflate displacement with grignard reagents, copper catalysed ether formation, metal catalysed amine aromatic substitution, aromatic carbonylation reaction; reaction on reactive groups such as acylation, alcoxycarbonylation of nitrogen containing groups such as amines, amidines, guanidines; substitution of hydroxy with nucleophile (Mitsunobu reaction or activation and nucleophilic substitution); hydrogenation of unsaturation (alkenyl to alkyl, alkynyl to alkenyl, alkynyl to alkyl); Staudinger reduction of azido group.

The process of the invention may comprise the additional step of isolating the desired compound of formula (II).

The starting products and/or reagents may be commercially available, or may be readily prepared by the skilled person by applying or adapting the procedures disclosed in the experimental part below.

According to a still further object, the present invention is also concerned with pharmaceutical compositions comprising a compound of formula (II) as defined above with a pharmaceutically acceptable excipient.

The compounds of the invention are dual antagonists and/or inverse agonists of H1R and H4R. The pharmaceutical compositions and compounds of the invention may thus be useful for use in the treatment and/or prevention of a disease associated with H1 and/or H4 dysfunction, such as inflammatory disorders.

Said disease includes adult respiratory distress syndrome, acute respiratory distress syndrome, bronchitis, chronic bronchitis, chronic obstructive pulmonary disease, cystic fibrosis, asthma, emphysema, rhinitis, chronic sinusitis, allergy, allergy induced airway responses, allergic rhinitis, viral rhinitis, non-allergic rhinitis, perennial and seasonal rhinitis, conjunctivitis, allergic conjunctivitis, ocular itching, chronic urticaria, eczema, prurigo, pruritus cutaneous, erythema exsudativum, nasal congestion, allergic congestion; disorders of the genito-urinary tract such as female and male sexual dysfunction, overactive bladder conditions, urinary incontinence, bladder over activity, benign prostate hyperplasia and lower urinary tract symptoms; dermatological diseases such as dermatitis, atopic dermatitis, and psoriasis and treatment of itchy skin; diseases of the cardiovascular system including thromboembolic diseases, atherosclerosis, myocardial infarction, angina pectoris, myocardial ischemia and arrhythmia, peripheral arterial occlusive diseases, pulmonary embolisms or deep venous thromboses, hypotension, pulmonary hypertension, malignant hypertension, cardiac insufficiency, heart or kidney failure, stroke and renal dysfunction; diseases of the gastrointestinal tract including inflammatory bowel disease, Crohn's disease, ulcerative colitis; autoimmune diseases including rheumatoid arthritis, multiple sclerosis; cancer; pain; lymphatic diseases.

According to a further object, the present invention also concerns a combination of a compound (II) of the invention with one or more therapeutic agent(s) selected from:
Histamine $H_1$, $H_2$ $H_3$ or $H_4$ receptor antagonists,
Leukotriene antagonists,
5-Lipoxygenase (5-LO) inhibitors or 5-lipoxygenase activating protein (FLAP) antagonists
$CX_1$- and $\alpha_2$-adrenoceptor agonist vasoconstrictor sympathomimetic agents for decongestant use
Xanthines, such as theophylline and aminophylline Non-steroidal antiinflammatories, such as sodium cromoglycate and nedocromil sodium
Ketotifen
COX-1 inhibitors (NSAIDs) and COX-2 selective inhibito
Immunosuppressants
mucolytics or anti-tussive agents More particularly, the present invention also concerns combinations comprising a compound of formula (II) of the invention with a H1R antagonist, such as cetirizine, desloratadine, bepotastine or doxepin.

According to a still further object, the present invention is also concerned with a compound of formula (II) for treating and/or preventing the above conditions.

According to a still further object, the present invention also concerns the methods of treatment comprising administering an effective amount of a compound (II) of the invention for treating and/or preventing the above conditions or disorders, to a patient in the need thereof.

The compounds of the present invention display interesting dual activity at H1 and H4 human receptors, a good safety margin, a good bioavailability and a good distribution profile.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propanoic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical*

Sciences, 17th ed., Mack Publishing Company, Easton, PA, 1985, p. 1418, the disclosure of which is hereby incorporated by reference.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (II), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day. A preferred daily dose for adult humans includes 1, 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably, the unit dose range is from 1 to 500 mg administered one to four times a day, and even more preferably from 1 mg to 300 mg, once a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches or ocular administration, or intravaginal or intra-uterine administration, particularly in the form of pessaries or by rectal administration.

The compositions may conveniently be administered in unit dosage form and may be prepared by any of the methods well known in the pharmaceutical art, for example, as described in Remington: The Science and Practice of Pharmacy, 20th ed.; Gennaro, A. R., Ed.; Lippincott Williams & Wilkins: Philadelphia, PA, 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally.

Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

BRIEF DESCRIPTION OF THE DRAWING FIGURES

Figure 1:
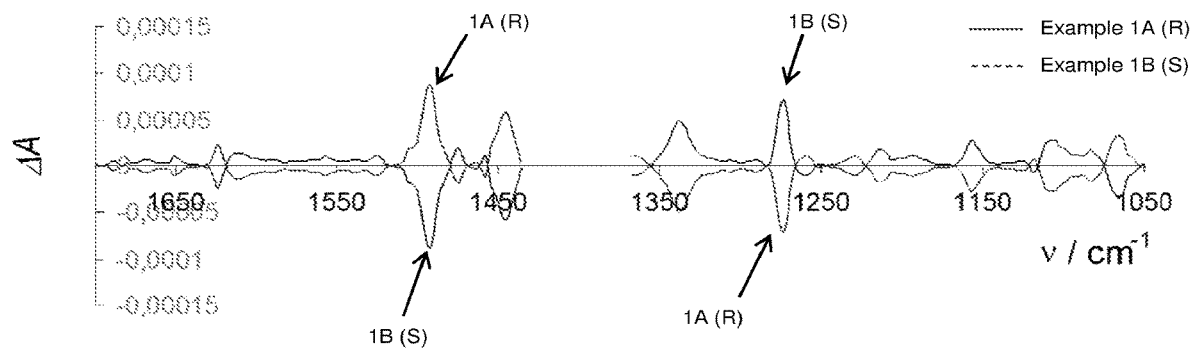
FIG. 1 is a VCD spectra of the two enantiomers of the racemic mixture of example 1 in $CD_2Cl_2$ (half-sum substracted).

Other features of the invention will become apparent in the course of the following description of exemplary embodiments that are given for illustration of the invention and not intended to be limiting thereof.

EXAMPLES

Melting points are determinate on Büchi capillary melting point apparatus.

Proton NMR spectra are recorded on a Varian 400 MHz NMR instrument. Deuterochloroform is used as solvent unless otherwise stated. The chemicals shifts δ are expressed in ppm. The following abbreviations are used to denote signal patterns: s=singlet, d=doublet, t=triplet, q=quadruplet, m=multiplet, ms=massif. The coupling contents are expressed in Hz. The spectra recorded are consistent with the proposed structures.

Example 1: (S)-2-[(1H-benzimidazol-2-yl)(1-methylpiperidin-4-yloxy)methyl]-6-fluorophenol Synthesis of racemic 2-[(1H-benzimidazol-2-yl)(1-methylpiperidin-4-yloxy)methyl]-6-fluorophenol has been described in patent application WO2012041860 (example 581).

To a solution of racemic 2-[(1H-benzimidazol-2-yl)(1-methylpiperidin-4-yloxy)methyl]-6-fluorophenol (6.52 g) in dichloromethane (180 mL) was added trimethylamine (2.86 mL) and (1S)-menthyl chloroformate (3.96 mL). The mixture was stirred at room temperature for 2 hours and then diluted with water. The organic phase was washed with brine, dried over magnesium sulfate and concentrated under reduced pressure. The residue was purified by preparative HPLC chromatography (Waters AutoPurification HPLC/MS System, Sunfire Prep C18 OBD 5 μm 30×150 mm column, eluents: water/0.1% formic acid (A) and acetonitrile/0.1% formic acid (B), isocratic elution with A/B 73/27 for 11 minutes then linear gradient to 5/95 in 4 minutes, sample diluted in methanol, multiple cycles). Fractions of the secondly eluted diastereomer (retention time of 13 minutes) were collected, treated with sodium bicarbonate and extracted with ethyl acetate. After drying over magnesium sulfate the organic phase was concentrated under reduced pressure. The residue was diluted with ethanol, treated with potassium hydroxide (2.0 g) in water (10 mL) for 30 minutes at room temperature. After pH adjustment around 8 with 3N aqueous HCl then aqueous sodium bicarbonate, extraction of the aqueous phase with ethyl acetate, drying of the pooled extracts over magnesium sulfate, and concentration under reduced pressure, the residue was purified by column chromatography over silica gel (gradient dichloromethane/methanol/ammonia from 95/5/0.5 to 90/10/0.5) to afford (S)-2-[(1H-benzimidazol-2-yl)(1-methylpiperidin-4-yloxy)methyl]-6-fluorophenol as a white powder displaying the following NMR spectrum: $^1$H NMR (MeOD): 7.52 (m, 2H), 7.20 (m, 2H), 7.16 (m, 1H), 7.02 (m, 1H), 6.79 (m, 1H), 6.25 (s, 1H), 3.59 (m, 1H), 2.74 (m, 2H), 2.25 (s, 3H), 2.20 (m, 2H), 1.95 (m, 2H), 1.78 (m, 2H). Exchangeable protons not reported.

Chiral HPLC analysis: analytical Chiralpak AD-H, 250× 4.6 mm column. Elution was performed with a mixture of heptane/isopropanol (95/5) containing diethylamine (0.1%) at a flow of 1 mL/min. The (S) enantiomer has a retention time of 27.7 minutes (retention time of (R) enantiomer=18.6 minutes). e.e.=100%.

Example 2: (S)-2-[(1H-benzimidazol-2-yl)(1-methylpiperidin-4-yloxy)methyl]-6-fluorophenol, Hydrochloride, Monohydrate A solution of (S)-2-[(1H-benzimidazol-2-yl)(1-methylpiperidin-4-yloxy)methyl]-6-fluorophenol (7.82 g) in acetone (100 mL) was treated with one equivalent of 37% hydrochloric acid at room temperature. After strong stirring for 3 hours, the solid was filtered, rinsed with acetone and dried under reduced pressure to afford 2-[(1H-benzimidazol-2-yl)(1-methylpiperidin-4-yloxy) methyl]-6-fluorophenol, hydrochloride, monohydrate as a white powder displaying the following NMR spectrum: 1H NMR (MeOD): 7.55 (m, 2H), 7.23 (m, 2H), 7.10 (m, 1H), 7.08 (m, 1H), 6.83 (m, 1H), 6.28 (s, 1H), 3.89 (m, 1H), 3.43-3.20 (ms, 4H), 2.84 (s, 3H), 2.20-1.90 (ms, 4H). Exchangeable protons not reported.

XRPD (major peaks, 2θ in °): 13.6, 15.1, 15.6, 16.4, 18.1, 20.3, 22.2, 27.6, 29.0

Example 3: (S)-2-[(5-chloro-4-fluoro-1H-benzimidazol-2-yl)(1-methylpiperidin-4-yloxy)methyl]phenol

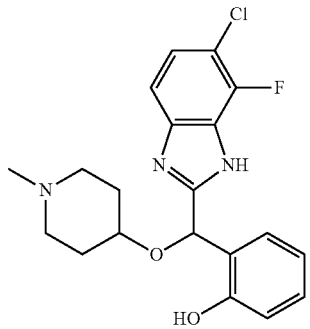 [SMILES: CN1CCC(OC(c2nc3ccc(Cl)c(F)c3[nH]2)c2ccccc2O)CC1]

3A

2-[(5-chloro-4-fluoro-1H-benzimidazol-2-yl)(1-methylpiperidin-4-loxy)methyl]phenol enantiomer B was prepared according to example 1 from racemic 2-[(5-chloro-4-fluoro-1H-benzimidazol-2-yl)(1-methylpiperidin-4-yloxy)methyl]phenol and derivatization with (1R)-menthyl chloroformate. During preparative HPLC the first eluted diastereomer was collected and then deprotected by potassium hydroxide treatment to afford 2-[(5-chloro-4-fluoro-1H-benzimidazol-2-yl)(1-methylpiperidin-4-yloxy)methyl]phenol enantiomer B as a white powder displaying the following NMR spectrum: 1H NMR (MeOD): 7.34 (m, 1H), 7.27 (m, 1H), 7.22 (m, 1H), 7.11 (m, 1H), 6.83 (m, 1H), 6.79 (m, 1H), 6.20 (s, 1H), 3.57 (m, 1H), 2.71 (m, 2H), 2.22 (s, 3H), 2.18 (m, 2H), 1.93 (m, 2H), 1.75 (m, 2H). Exchangeable protons not reported.

Chiral HPLC analysis: analytical Chiralpak AD-H, 250× 4.6 mm column. Elution was performed with a mixture of heptane/isopropanol (93/7) containing diethylamine (0.1%) at a flow of 1 mL/min. The enantiomer B has a retention time of 12.6 minutes (retention time of enantiomer A=8.9 minutes). e.e.=99%.3B A mixture of 2-[(5-chloro-4-fluoro-1H-benzimidazol-2-yl)hydroxymethyl]phenol (6.48 g), 4-hydroxy-1-methylpiperidine (12.75 g) and para-toluenesulfonic acid monohydrate (29.5 g) in toluene (350 mL) and N-methylpyrrolidone (35 mL) was heated under reflux until complete conversion (1.5 hours) with a Dean Stark apparatus. Water was then added and the mixture stirred vigorously. After filtration of insoluble material and pH adjustment around 9, the aqueous phase was extracted several times with ethyl acetate. Reunited organic phases were washed with brine, dried over magnesium sulfate and concentrated under reduced pressure. The residue was purified by column chromatography over silica gel (gradient dichloromethane/methanol/ammonia from 95/5/0.5 to 90/10/0.5) to afford racemic 2-[(5-chloro-4-fluoro-1H-benzimidazol-2-yl)(1-methylpiperidin-4-yloxy)methyl]phenol as an off-white solid melting at 144° C.

3C

To a solution of 5-chloro-4-fluoro-1-(pyrrolidin-1-ylmethyl)-1H-benzimidazole (5.50 g) in tetrahydrofurane (30 mL) at −78° C. was added a 2M solution of lithium diisopropylamide (19.4 mL) and stirred for 2 hours at this temperature. A cooled mixture of salicylaldehyde (4.58 g) and 2M solution of lithium diisopropylamide (20 mL) in tetrahydrofurane (30 mL) was then added. The mixture was stirred for 50 minutes at −78° C. and allowed to warm to −10° C. over 15 minutes. After hydrolysis with aqueous saturated ammonium chloride and pH adjustment around 6 with concentrated hydrochloric acid the organic phase was washed with brine, dried over magnesium sulfate and concentrated under reduced pressure. The residue was purified by reflux in dichloromethane for 15 minutes. After cooling the solid was filtered to afford. 2-[(5-chloro-4-fluoro-1H-benzimidazol-2-yl)hydroxymethyl]phenol.

3D

A solution of 5-chloro-4-fluoro-1H-benzimidazole (10.7 g), pyrrolidine (4.68 g), and formaldehyde (37% in water, 5.85 g) in ethanol (100 mL) was refluxed for 100 minutes. After concentration under reduced pressure the residue was diluted with dichloromethane, dried over magnesium sulfate and concentrated under reduced pressure to afford 5-chloro-4-fluoro-1-(pyrrolidin-1-ylmethyl)-1H-benzimidazole.

3E

A mixture of 4-chloro-3-fluorobenzene-1,2-diamine (13.9 g) and formic acid (6.84 g) was stirred at 95° C. for 35 minutes. After cooling the mixture was diluted with water and ethyl acetate and acidified to pH 1-2. After filtration the aqueous phase was washed with ethyl acetate, basified to pH 9-10 with sodium hydroxide and extracted with ethyl acetate. Pooled extracts were dried over magnesium sulfate and concentrated under reduced pressure. The residue was purified by recrystallization in dichloromethane to afford 5-chloro-4-fluoro-1H-benzimidazole.

Example 4: (S)-2-[(4-methyl-1H-benzimidazol-2-yl)(1-methylpiperidin-4-loxy)methyl]phenol

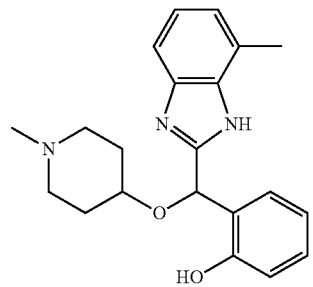 [SMILES: Cc1cccc2nc(C(OC3CCN(C)CC3)c3ccccc3O)[nH]c12]

4A

2-[(4-methyl-1H-benzimidazol-2-yl)(1-methylpiperidin-4-yloxy)methyl]phenol enantiomer B was prepared according to example 1 from racemic 2-[(4-methyl-1H-benzimidazol-2-yl)(1-methylpiperidin-4-yloxy)methyl]phenol and derivatization with (1S)-menthyl chloroformate. During preparative HPLC the second eluted diastereomer was collected and then deprotected by potassium hydroxide treatment to afford 2-[(4-methyl-1H-benzimidazol-2-yl)(1-methylpiperidin-4-yloxy)methyl]phenol enantiomer B as a white powder displaying the following NMR spectrum: 1H NMR (MeOD): 7.33 (m, 2H), 7.13 (m, 1H), 7.09 (m, 1H), 6.96 (m, 1H), 6.81 (m, 1H), 6.79 (m, 1H), 6.21 (s, 1H), 3.56 (m, 1H), 2.70 (m, 2H), 2.53 (s, 3H), 2.21 (s, 3H), 2.17 (m, 2H), 1.92 (m, 2H), 1.74 (m, 2H). Exchangeable protons not reported.

Chiral HPLC analysis: analytical Chiralpak AD-H, 250× 4.6 mm column. Elution was performed with a mixture of heptane/isopropanol (90/10) containing diethylamine (0.1%) at a flow of 1 mL/min. The enantiomer B has a retention time of 8.4 minutes (retention time of enantiomer A=7.2 minutes). e.e.=98%.

4B

Racemic 2-[(4-methyl-1H-benzimidazol-2-yl)(1-methylpiperidin-4-yloxy)methyl]phenol was prepared analogously to procedures 3B, 3C, 3D, and 3E starting from 2,3-diaminotoluene.

Example 5: (S)-2-[(5-fluoro-1H-benzimidazol-2-yl)(1-methylpiperidin-4-yloxy)methyl]phenol

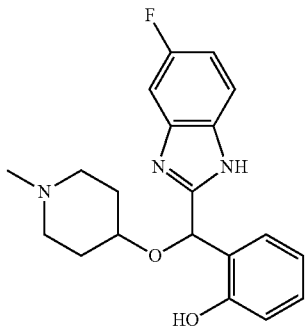 [SMILES: CN1CCC(OC(c2nc3cc(F)ccc3[nH]2)c2ccccc2O)CC1]

5A

2-[(5-fluoro-1H-benzimidazol-2-yl)(1-methylpiperidin-4-yloxy)methyl]phenol enantiomer B was prepared according to example 1 from racemic 2-[(5-fluoro-1H-benzimidazol-2-yl)(1-methylpiperidin-4-yloxy)methyl]phenol and derivatization with (1S)-menthyl chloroformate. During preparative HPLC the second eluted diastereomer was collected and then deprotected by potassium hydroxide treatment to afford 2-[(5-fluoro-1H-benzimidazol-2-yl)(1-methylpiperidin-4-yloxy)methyl]phenol enantiomer B as a white powder displaying the following NMR spectrum: 1H NMR (MeOD): 7.46 (m, 1H), 7.32 (d, 1H), 7.20 (m, 1H), 7.12 (m, 1H), 6.96 (m, 1H), 6.80 (m, 2H), 6.19 (s, 1H), 3.56 (m, 1H), 2.73 (m, 2H), 2.23 (s, 3H), 2.20 (m, 2H), 1.93 (m, 2H), 1.75 (m, 2H). Exchangeable protons not reported.

Chiral HPLC analysis: analytical Chiralpak AD-H, 250× 4.6 mm column. Elution was performed with a mixture of heptane/isopropanol (90/10) containing diethylamine (0.1%) at a flow of 1 mL/min. The enantiomer B has a retention time of 15.6 minutes (retention time of enantiomer A=9.5 minutes). e.e.=97%.

5B

Racemic 2-[(5-fluoro-1H-benzimidazol-2-yl)(1-methylpiperidin-4-yloxy)methyl]phenol was prepared analogously to procedures 3B, 3C, 3D, and 3E starting from 1,2-diamino-4-fluorobenzene.

Example 6: (S)-2-[(4-chloro-1H-benzimidazol-2-yl)(1-methylpiperidin-4-yloxy)methyl]phenol

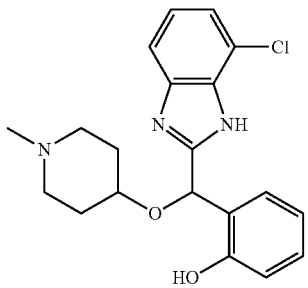 [SMILES: CN1CCC(OC(c2nc3cccc(Cl)c3[nH]2)c2ccccc2O)CC1]

6A

2-[(4-chloro-1H-benzimidazol-2-yl)(1-methylpiperidin-4-yloxy)methyl]phenol enantiomer B was prepared according to example 1 from racemic 2-[(4-chloro-1H-benzimidazol-2-yl)(1-methylpiperidin-4-yloxy)methyl]phenol and derivatization with (1S)-menthyl chloroformate. During preparative HPLC the second eluted diastereomer was collected and then deprotected by potassium hydroxide treatment to afford 2-[(4-chloro-1H-benzimidazol-2-yl)(1-methylpiperidin-4-yloxy)methyl]phenol enantiomer B as a white powder displaying the following NMR spectrum: 1H NMR (MeOD): 7.43 (d, 1H), 7.34 (d, 1H), 7.21-7.10 (ms, 3H), 6.85-6.78 (ms, 2H), 6.22 (s, 1H), 3.59 (m, 1H), 2.74 (m, 2H), 2.24 (s, 3H), 2.22 (m, 2H), 1.93 (m, 2H), 1.76 (m, 2H). Exchangeable protons not reported.

Chiral HPLC analysis: analytical Chiralpak AD-H, 250× 4.6 mm column. Elution was performed with a mixture of heptane/isopropanol (80/20) containing diethylamine (0.1%) at a flow of 1 mL/min. The enantiomer B has a retention time of 5.0 minutes (retention time of enantiomer A=4.5 minutes). e.e.=97%.

6B

Racemic 2-[(4-chloro-1H-benzimidazol-2-yl)(1-methylpiperidin-4-yloxy)methyl]phenol was prepared analogously to procedures 3B, 3C, 3D, and 3E starting from 2,3-diaminochlorobenzene.

Example 7: (S)-2-[(5-chloro-4-methyl-1H-benzimidazol-2-yl)(1-methylpiperidin-4-yloxy)methyl]phenol

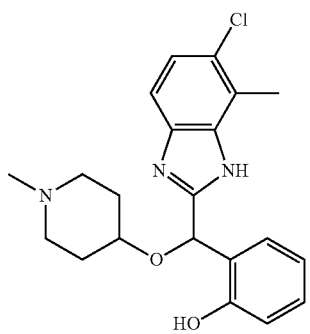 [SMILES: Cc1c(Cl)ccc2nc(C(OC3CCN(C)CC3)c3ccccc3O)[nH]c12]

7A

2-[(5-chloro-4-methyl-1H-benzimidazol-2-yl)(1-methylpiperidin-4-yloxy)methyl]phenol enantiomer B was prepared according to example 1 from racemic 2-[(5-chloro-4-methyl-1H-benzimidazol-2-yl)(1-methylpiperidin-4-yloxy)methyl]phenol and derivatization with (1R)-menthyl chloroformate. During preparative HPLC the first eluted diastereomer was collected and then deprotected by potassium hydroxide treatment to afford 2-[(5-chloro-4-methyl-1H-benzimidazol-2-yl)(1-methylpiperidin-4-yloxy)methyl] phenol enantiomer B as a white powder displaying the following NMR spectrum: 1H NMR (MeOD): 7.33 (d, 1H), 7.30 (d, 1H), 7.18 (d, 1H), 7.12 (m, 1H), 6.83-6.78 (ms, 2H), 6.21 (s, 1H), 3.56 (m, 1H), 2.72 (m, 2H), 2.56 (s, 3H), 2.22 (s, 3H), 2.17 (m, 2H), 1.92 (m, 2H), 1.76 (m, 2H). Exchangeable protons not reported.

Chiral HPLC analysis: analytical Chiralpak AD-H, 250× 4.6 mm column. Elution was performed with a mixture of heptane/isopropanol (95/5) containing diethylamine (0.1%) at a flow of 1 mL/min. The enantiomer B has a retention time of 13.9 minutes (retention time of enantiomer A=12.2 minutes). e.e.=97%.

7B

Racemic 2-[(5-chloro-4-methyl-1H-benzimidazol-2-yl)(1-methylpiperidin-4-loxy)methyl]phenol was prepared analogously to procedures 3B, 3C, 3D, and 3E starting from 6-chloro-2,3-diaminotoluene.

Example 8: (S)-2-[(1H-benzimidazol-2-yl)(1-methylpiperidin-4-yloxy)methyl]-6-fluorophenol, hydrochloride About 2900 ml of acetone and 112 g of (S)-2-[(1H-benzimidazol-2-yl)(1-methylpiperidin-4-yloxy)methyl]-6-fluorophenol (base) were charged into the reaction vessel. Mixture was warmed up to about 40° C. and agitated until starting material was dissolved and solution was filtered to remove the undissolved/foreign particles. Temperature of filtrate was adjusted to about 30° C. and about 47.5 g of HCl/MeOH (assay 26.4%, 1.1 equivalents) was added during 15-25 min at 32-34° C. Mixture was agitated for 1-2 h, filtered at 25-30° C. and washed with about 1000 ml of acetone. Five batches were finally combined by agitating them at room temperature with 1750 ml of acetone for about one hour. Product was filtered and washed with 250 ml of acetone. Finally, product was dried under reduced pressure at 45° C.

Enantiomeric purity determined by chiral HPLC (same as example 1): 99.8%

Assay by titration: 99.3%

Acetone content by GC head space: 0.3%

XRPD (major peaks, 2θ in °): 8.6, 12.4, 13.1, 15.9, 16.8, 19.9, 20.4, 21.3, 23.4, 25.0, 25.7, 26.3, 26.9, 28.4, 30.1

Example 9: (S)-2-[(1H-benzimidazol-2-yl)(1-methylpiperidin-4-yloxy)methyl]-6-fluorophenol, (R)-para-methylmandelate A suspension of racemic 2-[(1H-benzimidazol-2-yl)(1-methylpiperidin-4-yloxy)methyl]-6-fluorophenol (64.7 g) in methanol (450 mL) was warmed to reflux and then treated with a solution of (R)-para-methylmandelic acid (18.1 g) in methanol (150 mL). After reflux for 2 hours the mixture was allowed to cool to room temperature and the white solid filtered. Several recrystallizations were performed to afford optically pure (S)-2-[(1H-benzimidazol-2-yl)(1-methylpiperidin-4-yloxy)methyl]-6-fluorophenol, (R)-para-methylmandelate displaying the following NMR spectrum: 1H NMR (DMSO-d6): 12.45 (large s, 1H), 7.50 (m, 2H), 7.25 (d, 2H), 7.20 (d, 1H), 7.14 (m, 2H), 7.12-7.06 (ms, 3H), 6.82 (m, 1H), 6.11 (s, 1H), 4.77 (s, 1H), 2.75 (m, 2H), 2.32-2.20 (ms, 8H), 1.87 (m, 2H), 1.63 (m, 2H). Exchangeable protons not reported.

Example 10: (S)-2-[(1H-benzimidazol-2-yl)(1-methylpiperidin-4-yloxy)methyl]-6-fluorophenol, Hydrochloride, Monohydrate (S)-2-[(1H-benzimidazol-2-yl)(1-methylpiperidin-4-yloxy)methyl]-6-fluorophenol, (R)-para-methylmandelate (36.7 g) was diluted in water and aqueous sodium hydroxide. Ethyl acetate was then added and pH adjusted to around 8.5. After extraction of the aqueous phase with ethyl acetate (5 times) pooled extracts were dried over magnesium sulfate and concentrated under reduced pressure to yield (S)-2-[(1H-benzimidazol-2-yl)(1-methylpiperidin-4-yloxy)methyl]-6-fluorophenol as an off-white solid. After treatment with acetone (330 mL) and concentrated hydrochloric acid (1 equivalent) and vigorous stirring for 3 hours, the formed solid was filtered, rinsed with acetone and dried under reduced pressure to afford (S)-2-[(1H-benzimidazol-2-yl)(1-methylpiperidin-4-yloxy)methyl]-6-fluorophenol, hydrochloride, monohydrate as a white solid displaying the following NMR spectrum: 1H NMR (MeOD): 7.55 (m, 2H), 7.23 (m, 2H), 7.10 (m, 1H), 7.08 (m, 1H), 6.83 (m, 1H), 6.28 (s, 1H), 3.89 (m, 1H), 3.43-3.20 (ms, 4H), 2.84 (s, 3H), 2.20-1.90 (ms, 4H). Exchangeable protons not reported.

XRPD (major peaks, 2θ in °): 6.3, 11.0, 13.7, 15.1, 15.7, 16.4, 18.1, 20.3, 22.1, 24.4, 27.6, and 29.1.

Figure 2:
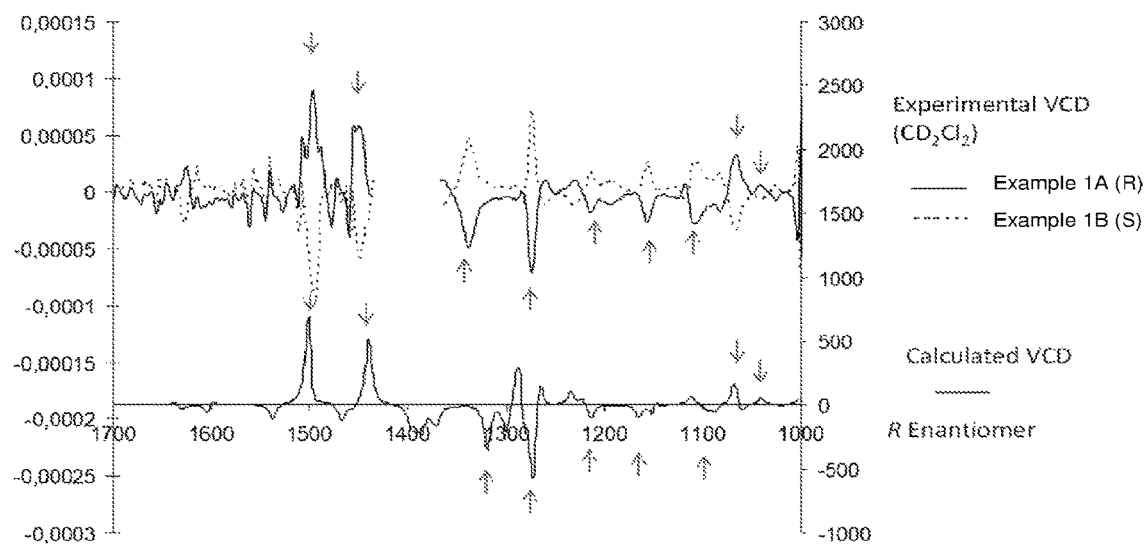
FIG. 2 illustrates the comparison of experimental VCD spectra of the two enantiomers of example 1 in $CD_2Cl_2$ (half-sum substracted) with the calculated one for conformer A2 (R enantiomer).

Example 11: Experimental Infrared (IR) and Vibrational Circular Dichroism (VCD) Measurements IR and VCD spectra were recorded on a FVS-6000 VCD spectrometer with 3000 scans collection, 4 cm-1 resolution, in the 1050-1700 cm-1 region. Samples of distomer of example 1 (20.8 mg in 400 µL CD2Cl2) and example 1 (14.06 mg in 300 µL CD2Cl2) were placed in a 200-µm pathlength cell with BaF2 windows. An overlay of the observed IR spectra for the two enantiomers is presented in FIG. 1; they show identical IR peaks with slightly higher intensity for distomer of example 1 due to higher concentration. In FIG. 2 are depicted the experimental VCD spectra for the two enantiomers example 1 and distomer of example 1 for which the solvent has been substracted. The VCD spectra exhibit the expected mirror-image relationship despite the sloping of the baseline. To eliminate possible artifacts and the sloping of the VCD baseline, the two VCD spectra have been substracted by the half-sum as shown in FIG. 1. The absorption region corresponding to the solvent has also been removed. These are two common operations.

VCD Calculations

Theoretical calculations have been conducted with the Gaussian 09 software. Vibrational circular dichroism spectra were obtained by TD-DFT using the B3LYP functional and the 6-311G(d,p) basis set.

The R enantiomer has been chosen for the calculations. The theoretical VCD spectra have been calculated for each possible conformer present. The conformational analysis revealed the presence of two major conformers denoted A2 and B, with respective 96.1 and 3.6% population. Four other conformers have been found but they correspond to less than 0.3% contribution and therefore have not been considered in the calculation.

For each conformer A2 and B, three steps have been conducted: i) optimisation by DFT with Gaussian 09—B3LYP-6-311G(d,p), ii) IR NCD calculation by TDDFT with Gaussian 09—B3LYP-6-311G(d,p), iii) the calculated frequencies have been multiplied by 0.97 to match the experimental ones.

The comparison of the theoretical VCD spectrum of the most populated conformer A2 with the experimental VCD ones is displayed in FIG. 2. The calculated spectrum matches very well the experimental one corresponding to the sample of distomer of example 1. The VCD peaks that have the same sign in the experiment and in the theory are highlighted with arrows.

The theoretical VCD spectrum of conformer B was compared with the experimental VCD spectra. The calculated spectrum matches with the experimental VCD spectrum of distomer of example 1 sample especially for the peaks highlighted with arrows. However, the matching is less good than for conformer A2.

Conclusion

The very good matching obtained by comparison of experimental VCD spectrum of enantiomer sample distomer of example 1 with the calculated VCD spectrum of the R enantiomer in its most populated (96%) conformation A2 enables to determine the absolute configuration R for distomer of example 1 and S for example 1 with good confidence. Furthermore, this VCD study confirms the fact that in a CD2Cl2 solution the molecule is exclusively present in its A2 conformation.

As a result, the absolute configuration of examples 1, 2, 8, 9, 10, and 12 is (S).

Example 12: Polymorphs

Many phases and polymorphs have been discovered for (S)-2-[(1H-benzimidazol-2-yl)(1-methylpiperidin-4-yloxy)methyl]-6-fluorophenol hydrochloride. The more stable phases are phase I which corresponds to an anhydrous hydrochloride and phase II which corresponds to a monohydrate of the hydrochloride.

The sample is analyzed by X-ray powder diffraction in transmission mode (the sample is placed between Kapton® and Polypropylene foils).

Scanning range 2-50°
Step size 0.026°
Acquisition time 20.4 s
Number of scans 20
The diffractometer is a X'Pert Pro MPD Panalytical. Characteristics of the beams are the followings:

| Incident Beam (Transmission Mode) | Radius (mm): 240.0 X-ray tube: Name PW3373/10 Anode Material: Cu Voltage (kV): 40 Current (mA): 40 Focus type: Line (Length (mm): 12.0 width (mm): 0.4 Take-off angle (°): 4.4 X-ray mirror Name: Inc. Beam Cu W/Si (parabolic MPD) Crystal (W/Si Graded Parabolic) Acceptance angle (°): 0.8 Length (mm): 55.3 Soller slit Soller 0.04 rad. Opening (rad.): 0.04 Anti-scatter slit: AS Slit 1.4 mm (mirror) Type: Fixed Height (mm): 1.40 Divergence slit Slit Fixed ⅛° Distance to sample (mm): 140 Type: Fixed Height (mm): 0.19 |
|---|---|
| Diffracted Beam | Radius (mm): 240.0 Soller slit Name: Large Soller 0.04 rad. Opening (rad.): 0.04 Detector Name: PIXcel Type: RTMS detector PHD - Lower level (%): 25.5 PHD - Upper level (%): 70.0 Mode: Scanning Active length (°): 3.347 |

Figure 3:
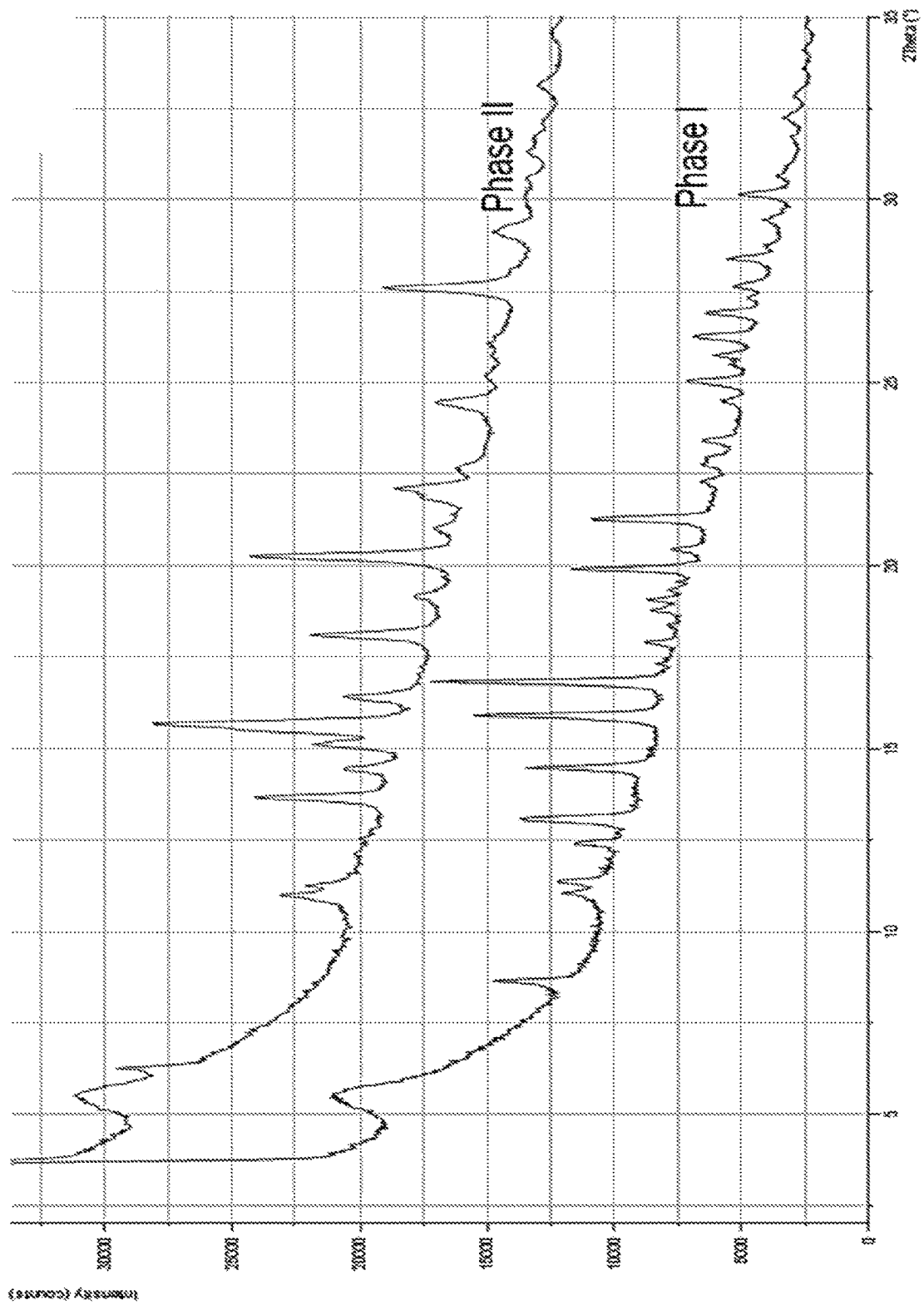
FIG. 3 shows the XRPD of phase I (anhydrous) and phase II (monohydrate) of (S)-2-[(1H-benzimidazol-2-yl)(1-methylpiperidin-4-yloxy)methyl]-6-fluorophenol, hydrochloride.

The X-ray powder diffraction patterns are displayed in FIG. 3.

XRPD allows a good characterization of these two phases.

Phases I and II comprise the following characterizing peaks by XRPD, respectively:

Phase I XRPD (characteristic peaks, 2θ in °): 8.6, 12.4, 13.1, 15.9, 16.8, 18.8, 19.9, 20.4, 21.3, 23.4, 25.0, 25.7, 26.3, 26.9, 28.4, and 30.1

Phase II XRPD (characteristic peaks, 2θ in °): 6.3, 13.7, 15.1, 15.7, 16.4, 20.3, 22.1, 24.4, and 29.1

Example 13: Biological Data

Example 13a: H1-H4 Binding

The above-mentioned property that the eutomer recognizes both receptors is shown in the table below. Activity at the human H1 receptor is determined by the inhibition of agonist-induced stimulation of radioactive GTP-gamma-S binding at recombinant receptors. The activity is reported as the constant Kb: the lowest, the most potent. Affinity for the human H4 receptor is determined by binding competition. The affinity is reported with the inhibition constant Ki: the lowest, the most potent.

| | | | hH1 GTPgS Kb (nM) | hH4 Binding Ki (nM) |
|---|---|---|---|---|
| Example 1 | Eutomer B(S) | | 2.18 | 5.02 |
| | Distomer A | | 225 | 788 |
| Example 7 | Eutomer B(S) | | 1.87 | 0.727 |
| | Distomer A | | 132 | 73.1 |
| Example 3 | Eutomer B(S) | | 1.43 | 0.61 |
| | Distomer A | | 156 | 42 |

| | | | hH1 GTPgS Kb (nM) | hH4 Binding Ki (nM) |
|---|---|---|---|---|
| Example 4 | Eutomer B(S) | [structure: 4-methylbenzimidazole with N-methylpiperidine-O-CH-phenyl-OH] | 0.165 | 2.87 |
| | Distomer A | | 133 | 491 |
| Example 5 | Eutomer B(S) | [structure: 5-fluorobenzimidazole with N-methylpiperidine-O-CH-phenyl-OH] | 1.65 | 0.915 |
| | Distomer A | | 97.5 | 249 |
| Example 6 | Eutomer B(S) | [structure: 4-chlorobenzimidazole with N-methylpiperidine-O-CH-phenyl-OH] | 1.25 | 3.42 |
| | Distomer A | | 598 | 474 |

It is usual that one enantiomer displays a better affinity for a receptor than its mirror image. However, it could not be predicted that the enantiomer which has the better affinity for the H4 receptor also has the better affinity for the H1 receptor. This totally unexpected property is of great interest as dual H1R-H4R receptor ligands have long been sought but none reached the clinics and only very few were disclosed. Finding equipotent dual H1R-H4R ligands is known to be a great challenge: 'As the amino acids forming the orthosteric binding pocket of hH1R and hH4R have smallest identity when comparing the human histamine receptors, it may be very challenging to develop ligands with similar affinity to hH1R and hH4R' (S. G. Hammer et al Bioorg. Med. Chem. Lett. 26; 2016; 292-300). The cited publication discloses ligand displaying micromolar affinity for both receptors. These extremely weak affinities render these compounds unsuitable for clinical development. The compounds of the present application display nanomolar affinities for both receptors i.e. thousand times more potent.

Example 13b: hERG Binding

Compounds that are antagonists or inverse agonists at the human H1 receptor are often found to bind to the hERG channel, giving rise to arrhythmia possibly leading to sudden cardiac arrest. This led to the withdrawal of several medicines from the clinics. This parameter has thus been evaluated for the compounds of the present application.

It has been surprisingly found that the above-mentioned eutomers represented by general formula (II) are the enantiomers that recognize the hERG channel with the lowest affinity. This property is totally unexpected as a recent publication showed that both enantiomer normally display the similar affinity for the hERG channel (Bagdanoff et al, J. Med. Chem., 2015, 58 (15), pp 5781-5788).

The discriminative recognition of hERG channel by the eutomer versus the distomer is shown in the table below where the reported values are the inhibition constant determined by competition binding:

| | | | hERG Binding Ki (nM) |
|---|---|---|---|
| Example 1 | Eutomer B(S) | [structure: benzimidazole with N-methylpiperidine-O-CH-phenyl(F)-OH] | 11400 |
| | Distomer A | | 4210 |
| Example 7 | Eutomer B(S) | [structure: chloro-methyl-benzimidazole with N-methylpiperidine-O-CH-phenyl-OH] | 3010 |
| | Distomer A | | 586 |
| Example 3 | Eutomer B(S) | [structure: chloro-fluoro-benzimidazole with N-methylpiperidine-O-CH-phenyl-OH] | 2580 |
| | Distomer A | | 783 |

-continued

| | | | hERG Binding Ki (nM) |
|---|---|---|---|
| Example 4 | Eutomer B(S) | 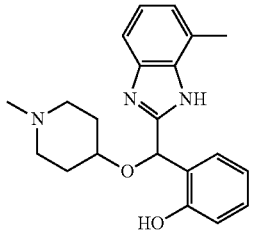 [SMILES: Cc1cccc2nc(C(OC3CCN(C)CC3)c3ccccc3O)[nH]c12] | 21300 |
| | Distomer A | | 2780 |
| Example 5 | Eutomer B(S) | 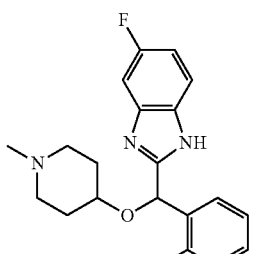 | 3210 |
| | Distomer A | | 646 |
| Example 6 | Eutomer B(S) | 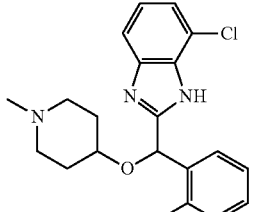 | 12500 |
| | Distomer A | | 1490 |

This property is not shared by closely structure-related compounds which are covered by general formula (I) of WO 2012/041860 but not encompassed by general formula (II) of the invention. This is shown in the table below:

Comparative compounds of WO 2012/041860:

| | | hERG Binding Ki (nM) |
|---|---|---|
| Eutomer | 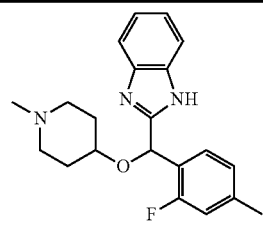 | 503 |
| Distomer | | 363 |

-continued

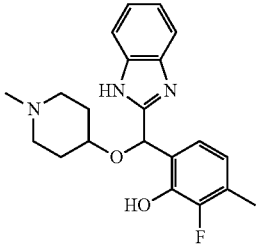

| | hERG Binding Ki (nM) |
|---|---|
| Eutomer | 3100 |
| Distomer | 5700 |
| Eutomer | 18000 |
| Distomer | 32000 |
| Eutomer | 220 |
| Distomer | 799 |
| Eutomer | 6680 |
| Distomer | 8430 |

The property that one single enantiomer recognizes both the human H1 receptor and the human H4 receptor together with a demonstrated trend to efficiently discriminate the hERG channel is thus totally unexpected and of great pharmaceutical interest.

As a result of these unexpected properties, the compounds of the present application display outstanding in vitro properties. They are potent antagonists or inverse agonists at both the H1 and H4 human histamine receptors with low nanomolar or subnanomolar affinities. They display a huge selectivity for these receptor against the hERG channel with ratios ranging from 1600 up to 129000. These properties are of paramount importance for medicinal products as they should lead to compounds with large safety margins.

Example 13c: In Vivo Studies

Brain Exposure:

Compounds that are acting as agonists or inverse agonists on the histamine H1 receptor should not enter the brain. This would lead to unwanted side effects such as sedation and weight gain. The efficiency for entering into the brain may be assessed by administrating the compound per os to mice and measuring the exposure over 8 hours in the brain and in the plasma. The result may be expressed by the ratio of the exposure in brain over the one in plasma.

This property has been compared for the compounds of the invention vs. some comparative compounds WO2012/041860:

Comparative compounds of WO2012/041860:

| example | dose mg/kg | ratio |
| --- | --- | --- |
| 1 | 10 | 13 |
| 11 | 10 | 13 |
| 25 | 10 | 8 |
| 26 | 10 | 8 |
| 41 | 10 | 17 |
| 45 | 10 | 2 |
| 53 | 1 | 52 |
| 88 | 10 | 4 |
| 111 | 10 | 12 |
| 321 | 10 | 3 |
| 337 | 10 | 41 |
| 409 | 10 | 12 |
| 618 | 10 | 1 |

Results of examples of the present invention are reported in the table below:

| example | dose mg/kg | ratio |
| --- | --- | --- |
| 1 | 10 | 0.2 |
| 3 | 1 | 0.0 |
| 4 | 1 | 0.3 |
| 6 | 1 | 0.0 |

The ratio of the exposure brain over plasma is clearly below 1 for the compounds of the invention. This shows that the present compounds do not enter significantly the brain. This property is a breakthrough in that it was not suggested previously, and is not shared by compounds of the patent application WO2012/041860 for which many compounds were found to largely enter the brain.

Bioavailability

Furthermore, compounds of the present invention were found to be bioavailable when administered per os to mice. Concentrations in lung were found to be interestingly high. This may be shown as cumulative exposure with the area under curve of the pharmacokinetics investigation as reported in the table below:

| example | dose mg/kg | lung AUC ng*h/g |
| --- | --- | --- |
| 1 | 10 | 20486 |
| 3 | 1 | 10037 |
| 4 | 1 | 1144 |
| 5 | 1 | 1264 |
| 6 | 1 | 6316 |
| 7 | 1 | 1169 |

These in vivo results show that the compounds of the present application are well absorbed, do not cross efficiently the blood brain barrier, but are efficiently distributed in therapeutically relevant organs such as lung.

What is claimed is:

1. A hydrochloride salt of an (S)-enantiomer of formula (II):

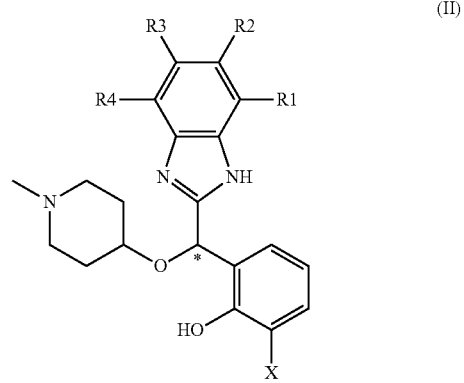

wherein:
* denotes the asymmetric carbon exhibiting a defined stereochemistry;
X represents F; and
R1, R2, R3, and R4 represent H;
wherein the hydrochloride salt of the (S)-enantiomer has dual affinity for H1 and H4 receptors, and
wherein the hydrochloride salt has the following X-ray powder diffraction peaks: (characteristic peaks, 2θ in°): 8.6, 12.4, 13.1, 15.9, 16.8, 18.8, 19.9, 20.4, 21.3, 23.4, 25.0, 25.7, 26.3, 26.9, 28.4, and 30.1.

2. A process for preparation of the hydrochloride salt of the (S)-enantiomer of formula (II) according to claim 1 comprising enantiomeric separation of the corresponding racemic mixture.

3. The process according to claim 2 wherein said racemate is prepared by:
either etherification of compound of formula (III):

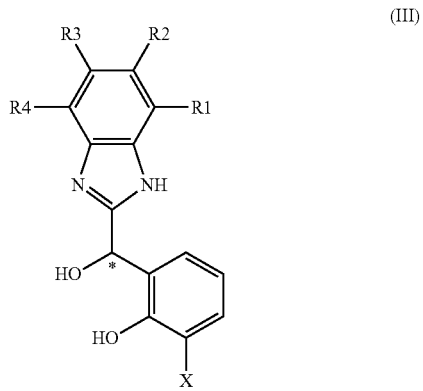

with a compound of formula (IV):

or methylation of compound of formula (V):

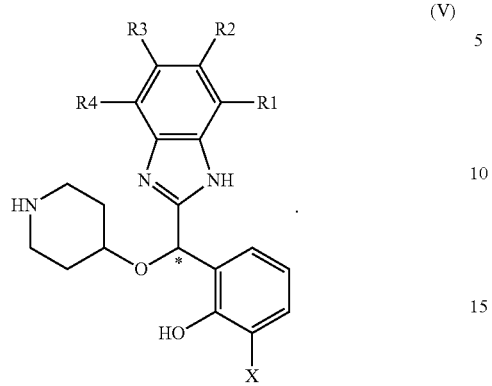

4. A pharmaceutical composition comprising the hydrochloride salt of the (S)-enantiomer according to claim 1 and a pharmaceutically acceptable excipient.

5. The pharmaceutical composition according to claim 4 for the treatment of an inflammatory disorder.

6. The pharmaceutical composition according to claim 5 where the inflammatory disorder is selected from the group consisting of anaphylactic shock, respiratory inflammatory and allergic diseases, adult respiratory distress syndrome, acute respiratory distress syndrome, respiratory infections, bronchitis, chronic bronchitis, chronic obstructive pulmonary disease, cystic fibrosis, asthma, emphysema, rhinitis, rhinorrhea, chronic sinusitis, allergy, allergy-induced airway responses, allergic rhinitis, viral rhinitis, non-allergic rhinitis, perennial and seasonal rhinitis, conjunctivitis, allergic conjunctivitis, otitis, nasal polyps, vaugh, ocular itching, chronic urticaria, eczema, prurigo, pruritus cutaneous, erythema exsudativum, nasal congestion, allergic congestion; disorders of the genito-urinary tract such as female and male sexual dysfunction, overactive bladder conditions, urinary incontinence, bladder overactivity, benign prostate hyperplasia and lower urinary tract symptoms; dermatological diseases such as dermatitis, atopic dermatitis, and psoriasis and itchy skin; pruritus, skin incision model of postoperative pain, allergic skin disease/itching and inflammation, allergic contact dermatitis, itching associated with hepatic or kidney insufficiency; diseases of the cardiovascular system including thromboembolic diseases, atherosclerosis, myocardial infarction, angina pectoris, myocardial ischemia, arrhythmia, peripheral arterial occlusive diseases, pulmonary embolisms deep venous thromboses, hypotension, pulmonary hypertension, angioedema, malignant hypertension, cardiac insufficiency, heart or kidney failure, stroke and renal dysfunction; diseases of the gastrointestinal tract including inflammatory bowel disease, Crohn's disease, ulcerative colitis; intestinal anaphylaxis, food allergy, post inflammatory visceral hypersensitivity, peritonitis, autoimmune diseases including rheumatoid arthritis, multiple sclerosis, lupus, osteoarthritis joint pain, general inflammation; cancer; pain, neuropathic pain, chronic hyper-eosinophilias, chronic diseases associated with mast cell multiplication; and lymphatic diseases.

7. A combination comprising the hydrochloride salt of the (S)-enantiomer according to claim 1 with an H1R antagonist.

8. The hydrochloride salt of claim 1 which is in anhydrous form.

9. The hydrochloride salt of claim 1 which is a monohydrate.

10. A hydrochloride salt of an (S)-enantiomer of formula (II):

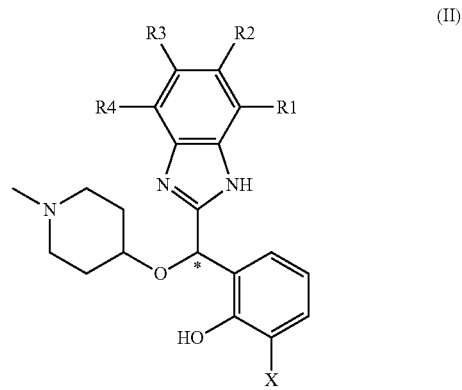

wherein:
* denotes the asymmetric carbon exhibiting a defined stereochemistry;
X represents F; and
R1, R2, R3, and R4 represent H;
wherein the hydrochloride salt of the (S)-enantiomer has dual affinity for H1 and H4 receptors, and
wherein the hydrochloride salt has the following X-ray powder diffraction peaks: (characteristic peaks, 2θ in°): 6.3, 13.7, 15.1, 15.7, 16.4, 20.3, 22.1, 24.4, and 29.1.

11. A process for preparation of the hydrochloride salt of the (S)-enantiomer of formula (II) according to claim 10 comprising enantiomeric separation of the corresponding racemic mixture.

12. The process according to claim 11 wherein said racemate is prepared by:
either etherification of compound of formula (III):

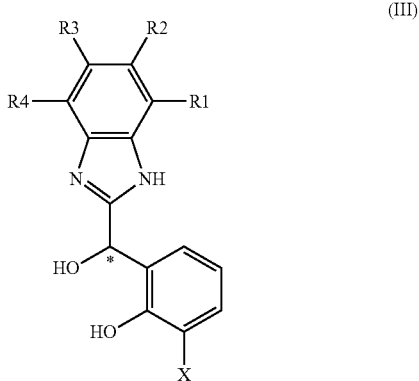

with a compound of formula (IV):

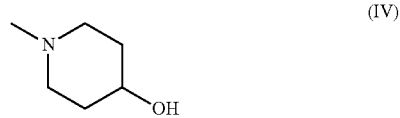

or methylation of compound of formula (V):

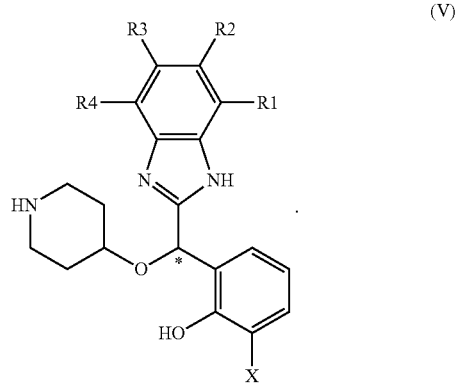

13. A pharmaceutical composition comprising the hydrochloride salt of the (S)-enantiomer according to claim 10 and a pharmaceutically acceptable excipient.

14. The pharmaceutical composition according to claim 13 for the treatment of an inflammatory disorder.

15. The pharmaceutical composition according to claim 14 where the inflammatory disorder is selected from the group consisting of anaphylactic shock, respiratory inflammatory and allergic diseases, adult respiratory distress syndrome, acute respiratory distress syndrome, respiratory infections, bronchitis, chronic bronchitis, chronic obstructive pulmonary disease, cystic fibrosis, asthma, emphysema, rhinitis, rhinorrhea, chronic sinusitis, allergy, allergy-induced airway responses, allergic rhinitis, viral rhinitis, nonallergic rhinitis, perennial and seasonal rhinitis, conjunctivitis, allergic conjunctivitis, otitis, nasal polyps, vaugh, ocular itching, chronic urticaria, eczema, prurigo, pruritus cutaneous, erythema exsudativum, nasal congestion, allergic congestion; disorders of the genito-urinary tract such as female and male sexual dysfunction, overactive bladder conditions, urinary incontinence, bladder overactivity, benign prostate hyperplasia and lower urinary tract symptoms; dermatological diseases such as dermatitis, atopic dermatitis, and psoriasis and itchy skin; pruritus, skin incision model of postoperative pain, allergic skin disease/itching and inflammation, allergic contact dermatitis, itching associated with hepatic or kidney insufficiency; diseases of the cardiovascular system including thromboembolic diseases, atherosclerosis, myocardial infarction, angina pectoris, myocardial ischemia, arrhythmia, peripheral arterial occlusive diseases, pulmonary embolisms deep venous thromboses, hypotension, pulmonary hypertension, angioedema, malignant hypertension, cardiac insufficiency, heart or kidney failure, stroke and renal dysfunction; diseases of the gastrointestinal tract including inflammatory bowel disease, Crohn's disease, ulcerative colitis; intestinal anaphylaxis, food allergy, post inflammatory visceral hypersensitivity, peritonitis, autoimmune diseases including rheumatoid arthritis, multiple sclerosis, lupus, osteoarthritis joint pain, general inflammation; cancer; pain, neuropathic pain, chronic hyper-eosinophilias, chronic diseases associated with mast cell multiplication; and lymphatic diseases.

16. A combination comprising the hydrochloride salt of the (S)-enantiomer according to claim 10 with an H1R antagonist.

17. The hydrochloride salt of claim 10 which is in anhydrous form.

18. The hydrochloride salt of claim 10 which is a monohydrate.

* * * * *